(12) United States Patent
Gueriguian et al.

(10) Patent No.: US 7,951,194 B2
(45) Date of Patent: May 31, 2011

(54) BIOABSORBABLE STENT WITH RADIOPAQUE COATING

(75) Inventors: Vincent J. Gueriguian, San Francisco, CA (US); Bin Huang, Pleasanton, CA (US); David C. Gale, San Jose, CA (US)

(73) Assignee: Abbott Cardiovascular Sysetms Inc., Santa Clara, CA (US)

( * ) Notice: Subject to any disclaimer, the term of this patent is extended or adjusted under 35 U.S.C. 154(b) by 180 days.

(21) Appl. No.: 11/805,357

(22) Filed: May 22, 2007

(65) Prior Publication Data

US 2008/0009939 A1 Jan. 10, 2008

Related U.S. Application Data

(60) Provisional application No. 60/809,072, filed on May 26, 2006.

(51) Int. Cl.
*A61F 2/06* (2006.01)

(52) U.S. Cl. ............ 623/1.44; 623/1.46; 623/1.42

(58) Field of Classification Search .......... 623/1.34, 623/1.38, 1.44, 1.48; 424/423
See application file for complete search history.

(56) References Cited

U.S. PATENT DOCUMENTS

| | | | |
|---|---|---|---|
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,800,882 A | 1/1989 | Gianturco | |
| 4,816,339 A | 3/1989 | Tu et al. | |
| 4,818,559 A | 4/1989 | Hama et al. | |
| 4,850,999 A | 7/1989 | Planck | |

(Continued)

FOREIGN PATENT DOCUMENTS

DE 44 07 079 9/1994

(Continued)

OTHER PUBLICATIONS

U.S. Appl. No. 10/317,435, filed Dec. 11, 2002, Hossainy et al.

(Continued)

*Primary Examiner* — David Isabella
*Assistant Examiner* — Seema Swaminathan
(74) *Attorney, Agent, or Firm* — Squire, Sanders & Dempsey (US) LLP (57) ABSTRACT

Various embodiments of stents with a bioabsorbable body having a coating with a radiopaque layer are disclosed.

7 Claims, 3 Drawing Sheets

U.S. PATENT DOCUMENTS

| | | |
|---|---|---|
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |

| | | | | | | |
|---|---|---|---|---|---|---|
| 6,080,488 | A | 6/2000 | Hostettler et al. | 6,592,614 B2 | 7/2003 | Lenker et al. |
| 6,083,258 | A | 7/2000 | Yadav | 6,592,617 B2 | 7/2003 | Thompson |
| 6,093,463 | A | 7/2000 | Thakrar | 6,613,072 B2 | 9/2003 | Lau et al. |
| 6,096,070 | A | 8/2000 | Ragheb et al. | 6,626,939 B1 | 9/2003 | Burnside et al. |
| 6,096,525 | A | 8/2000 | Patnaik | 6,635,269 B1 | 10/2003 | Jennissen |
| 6,099,562 | A | 8/2000 | Ding et al. | 6,645,243 B2 | 11/2003 | Vallana et al. |
| 6,103,230 | A | 8/2000 | Billiar et al. | 6,656,162 B2 | 12/2003 | Santini, Jr. et al. |
| 6,107,416 | A | 8/2000 | Patnaik et al. | 6,664,335 B2 | 12/2003 | Krishnan |
| 6,110,188 | A | 8/2000 | Narciso, Jr. | 6,666,214 B2 | 12/2003 | Canham |
| 6,113,629 | A | 9/2000 | Ken | 6,667,049 B2 | 12/2003 | Janas et al. |
| 6,117,979 | A | 9/2000 | Hendriks et al. | 6,669,723 B2 | 12/2003 | Killion et al. |
| 6,120,536 | A | 9/2000 | Ding et al. | 6,676,697 B1 | 1/2004 | Richter |
| 6,120,904 | A | 9/2000 | Hostettler et al. | 6,679,980 B1 | 1/2004 | Andreacchi |
| 6,121,027 | A | 9/2000 | Clapper et al. | 6,689,375 B1 | 2/2004 | Wahlig et al. |
| 6,125,523 | A | 10/2000 | Brown et al. | 6,695,920 B1 | 2/2004 | Pacetti et al. |
| 6,127,173 | A | 10/2000 | Eckstein et al. | 6,706,273 B1 | 3/2004 | Roessler |
| 6,129,761 | A | 10/2000 | Hubbell | 6,709,379 B1 | 3/2004 | Brandau et al. |
| 6,129,928 | A | 10/2000 | Sarangapani et al. | 6,719,934 B2 | 4/2004 | Stinson |
| 6,150,630 | A | 11/2000 | Perry et al. | 6,719,989 B1 | 4/2004 | Matsushima et al. |
| 6,153,252 | A | 11/2000 | Hossainy et al. | 6,720,402 B2 | 4/2004 | Langer et al. |
| 4,776,337 | A | 12/2000 | Palmaz | 6,736,842 B2 * | 5/2004 | Healy et al. .................. 623/1.15 |
| 6,159,951 | A | 12/2000 | Karpeisky et al. | 6,746,773 B2 | 6/2004 | Llanos et al. |
| 6,160,084 | A | 12/2000 | Langer et al. | 6,752,826 B2 | 6/2004 | Holloway et al. |
| 6,165,212 | A | 12/2000 | Dereume et al. | 6,753,007 B2 | 6/2004 | Haggard et al. |
| 6,166,130 | A | 12/2000 | Rhee et al. | 6,764,505 B1 | 7/2004 | Hossainy et al. |
| 6,169,170 | B1 | 1/2001 | Gryaznov et al. | 6,818,063 B1 | 11/2004 | Kerrigan |
| 6,171,609 | B1 | 1/2001 | Kunz | 6,846,323 B2 | 1/2005 | Yip et al. |
| 6,174,330 | B1 | 1/2001 | Stinson | 7,166,099 B2 | 1/2007 | Devens, Jr. |
| 6,177,523 | B1 | 1/2001 | Reich et al. | 7,476,889 B2 * | 1/2009 | DeMeo et al. ............. 250/516.1 |
| 6,183,505 | B1 | 2/2001 | Mohn, Jr. et al. | 2001/0044652 A1 | 11/2001 | Moore |
| 6,187,045 | B1 | 2/2001 | Fehring et al. | 2002/0002399 A1 | 1/2002 | Huxel et al. |
| 6,210,715 | B1 | 4/2001 | Starling et al. | 2002/0004060 A1 | 1/2002 | Heublein et al. |
| 6,224,626 | B1 | 5/2001 | Steinke | 2002/0004101 A1 | 1/2002 | Ding et al. |
| 6,228,845 | B1 | 5/2001 | Donovan et al. | 2002/0062148 A1 | 5/2002 | Hart |
| 6,240,616 | B1 | 6/2001 | Yan | 2002/0065553 A1 | 5/2002 | Weber |
| 6,241,719 | B1 | 6/2001 | Wallace et al. | 2002/0111590 A1 | 8/2002 | Davila et al. |
| 6,245,076 | B1 | 6/2001 | Yan | 2002/0116050 A1 | 8/2002 | Kocur |
| 6,245,103 | B1 | 6/2001 | Stinson | 2002/0138133 A1 | 9/2002 | Lenz et al. |
| 6,248,344 | B1 | 6/2001 | Ylanen et al. | 2002/0161114 A1 | 10/2002 | Gunatillake et al. |
| 6,251,135 | B1 | 6/2001 | Stinson et al. | 2003/0033001 A1 | 2/2003 | Igaki |
| 6,251,142 | B1 | 6/2001 | Bernacca et al. | 2003/0065355 A1 | 4/2003 | Weber |
| 6,273,913 | B1 | 8/2001 | Wright et al. | 2003/0093107 A1 | 5/2003 | Parsonage et al. |
| 6,281,262 | B1 | 8/2001 | Shikinami | 2003/0100865 A1 | 5/2003 | Santini, Jr. et al. |
| 6,284,333 | B1 | 9/2001 | Wang et al. | 2003/0105518 A1 | 6/2003 | Dutta |
| 6,287,332 | B1 | 9/2001 | Bolz et al. | 2003/0105530 A1 | 6/2003 | Pirhonen |
| 6,290,721 | B1 | 9/2001 | Heath | 2003/0171053 A1 | 9/2003 | Sanders |
| 6,293,966 | B1 | 9/2001 | Frantzen | 2003/0187495 A1 | 10/2003 | Cully et al. |
| 6,303,901 | B1 | 10/2001 | Perry et al. | 2003/0208259 A1 | 11/2003 | Penhasi |
| 6,312,459 | B1 | 11/2001 | Huang et al. | 2003/0209835 A1 | 11/2003 | Chun et al. |
| 6,327,772 | B1 | 12/2001 | Zadno-Azizi et al. | 2003/0224033 A1 | 12/2003 | Li et al. |
| 4,733,665 | C2 | 1/2002 | Palmaz | 2003/0226833 A1 | 12/2003 | Shapovalov et al. |
| 6,355,058 | B1 * | 3/2002 | Pacetti et al. ................. 623/1.15 | 2003/0236565 A1 | 12/2003 | Fifer |
| 6,375,826 | B1 | 4/2002 | Wang et al. | 2004/0093077 A1 | 5/2004 | White et al. |
| 6,379,381 | B1 | 4/2002 | Hossainy et al. | 2004/0098095 A1 | 5/2004 | Burnside et al. |
| 6,387,121 | B1 | 5/2002 | Alt | 2004/0111149 A1 | 6/2004 | Stinson |
| 6,388,043 | B1 | 5/2002 | Langer et al. | 2004/0127970 A1 | 7/2004 | Weber |
| 6,395,326 | B1 | 5/2002 | Castro et al. | 2004/0143317 A1 | 7/2004 | Stinson et al. |
| 6,409,761 | B1 | 6/2002 | Jang | 2004/0167610 A1 | 8/2004 | Fleming, III |
| 6,423,092 | B2 | 7/2002 | Datta et al. | 2005/0010275 A1 | 1/2005 | Sahatjian et al. |
| 6,461,632 | B1 | 10/2002 | Gogolewski | 2005/0036946 A1 | 2/2005 | Pathak et al. |
| 6,464,720 | B2 | 10/2002 | Boatman et al. | 2005/0149173 A1 | 7/2005 | Hunter et al. |
| 6,479,565 | B1 | 11/2002 | Stanley | 2005/0180919 A1 | 8/2005 | Tedeschi |
| 6,485,512 | B1 | 11/2002 | Cheng | 2008/0319539 A1 * | 12/2008 | Gellman et al. ............. 623/1.44 |
| 6,492,615 | B1 | 12/2002 | Flanagan | | | |
| 6,494,908 | B1 | 12/2002 | Huxel et al. | FOREIGN PATENT DOCUMENTS | | |
| 6,495,156 | B2 | 12/2002 | Wenz et al. | DE | 197 31 021 | 1/1999 |
| 6,511,748 | B1 | 1/2003 | Barrows | DE | 198 56 983 | 12/1999 |
| 6,517,888 | B1 | 2/2003 | Weber | EP | 0 108 171 | 5/1984 |
| 6,527,801 | B1 | 3/2003 | Dutta | EP | 0 144 534 | 6/1985 |
| 6,537,589 | B1 | 3/2003 | Chae et al. | EP | 0 364 787 | 4/1990 |
| 6,539,607 | B1 | 4/2003 | Fehring et al. | EP | 0 397 500 | 11/1990 |
| 6,540,777 | B2 | 4/2003 | Stenzel | EP | 0 464 755 | 1/1992 |
| 6,554,854 | B1 | 4/2003 | Flanagan | EP | 0 493 788 | 7/1992 |
| 6,565,599 | B1 | 5/2003 | Hong et al. | EP | 0 554 082 | 8/1993 |
| 6,569,191 | B1 | 5/2003 | Hogan | EP | 0 578 998 | 1/1994 |
| 6,569,193 | B1 | 5/2003 | Cox et al. | EP | 0 604 022 | 6/1994 |
| 6,572,672 | B2 | 6/2003 | Yadav et al. | EP | 0 621 017 | 10/1994 |
| 6,574,851 | B1 | 6/2003 | Mirizzi | EP | 0 623 354 | 11/1994 |
| 6,585,755 | B2 | 7/2003 | Jackson et al. | EP | 0 665 023 | 8/1995 |

| EP | 0 709 068 | 5/1996 |
| EP | 0 894 503 | 2/1999 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |
| WO | WO 2006/063106 | 6/2006 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives, a companion to the Handbook of Coronary Stents*, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et at, *Synthetic biodegradable polymers as orthopedic devices*, Biomaterials, vol. 21, pp. 2335-2346 (2000).

Muller et,al., *Advances in Coronary Angioplasty: Endovascular Stents*, Coron. Arter. Dis.,vol. 1(4), pp. 438-448 (Jul./Aug. 1990).

nanoComposix, products, www.nanocomosix.com, dowhloaded Mar. 26, 2007, 2 pgs.

Nanosiliver, Photocatalyst and Nanocomposite Material, http://eng.nanocomposite.net downloaded Mar. 26, 2007, 1 pg.

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et.al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single-chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

International Search Report for PCT/US2007/012482, mailed Aug. 8, 2008, 6 pgs.

\* cited by examiner

BIOABSORBABLE STENT WITH RADIOPAQUE COATING

CROSS REFERENCE TO RELATED APPLICATION

This application claims benefit of and incorporates by reference U.S. patent application Ser. No. 60/809,072, which was filed on May 26, 2006.

BACKGROUND OF THE INVENTION

1. Field of the Invention

This invention relates to implantable medical devices, such as stents. In particular, the invention relates to bioabsorbable polymeric stents with a radiopaque coating.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The structure of stents is typically composed of scaffolding that includes a pattern or network of interconnecting structural elements or struts. The scaffolding can be formed from wires, tubes, or sheets of material rolled into a cylindrical shape. In addition, a medicated stent may be fabricated by coating the surface of either a metallic or polymeric scaffolding with a polymeric carrier. The polymeric scaffolding may also serve as a carrier of an active agent or drug.

The first step in treatment of a diseased site with a stent is locating a region that may require treatment such as a suspected lesion in a vessel, typically by obtaining an x-ray image of the vessel. To obtain an image, a contrast agent, which contains a radiopaque substance such as iodine is injected into a vessel. "Radiopaque" refers to the ability of a substance to absorb x-rays. The x-ray image depicts the lumen of the vessel from which a physician can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion, which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is desirable for a stent to be radiopaque, or fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials may be configured to meet this additional clinical requirement since they may be designed to completely erode after the clinical need for them has ended. Stents fabricated from biodegradable polymers are particularly promising, in part because they may be designed to completely erode within a desired time frame.

However, a significant shortcoming of biodegradable polymers (and polymers generally composed of carbon, hydrogen, oxygen, and nitrogen) is that they are radiolucent with no radiopacity. Biodegradable polymers tend to have x-ray absorption similar to body tissue.

SUMMARY OF THE INVENTION

Various embodiments of the present invention include a stent comprising: a bioabsorbable polymer body; and a coating above the bioabsorbable body, the coating comprising a radiopaque layer including a radiopaque agent dispersed within a second bioabsorbable polymer.

Further embodiments, of the present invention include a stent comprising: a bioabsorbable polymer body; and a coating above the bioabsorbable body, the coating comprising a radiopaque layer, wherein a majority of the radiopaque layer comprises a water soluble contrast agent.

DETAILED DESCRIPTION OF THE INVENTION

The present invention may be applied to stents and, more generally, to implantable medical devices such as, but not limited to, self-expandable stents, balloon-expandable stents, stent-grafts, vascular grafts, or generally, tubular implantable medical devices.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent.

Figure 1:
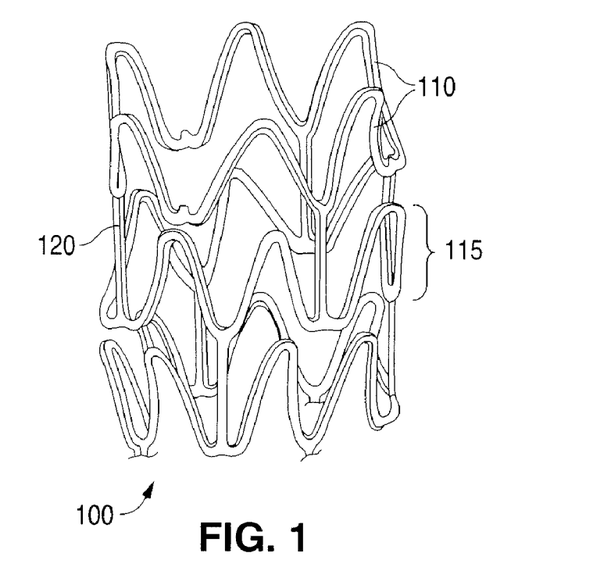
FIG. 1 depicts an exemplary stent.

FIG. 1 depicts an exemplary stent 100 with struts 110 that form cylindrical rings 115 which are connected by linking struts 120. The cross-section of the struts in stent 100 is rectangular-shaped. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

A stent can be made of a biostable, bioabsorbable polymer, or both. In general, polymers can be biostable, bioabsorbable, biodegradable, bioerodable, dissolvable, or water soluble. Biostable refers to polymers that are not bioabsorbable. The terms biodegradable, bioabsorbable, and bioerodable, biosoluble, as well as degraded, eroded, absorbed, and dissolved refer to polymers that are capable of being completely eroded or absorbed when exposed to bodily fluids such as blood and can be gradually resorbed, absorbed and/or eliminated by the body.

Some bioabsorbable polymers absorb due to chemical degradation that occurs in a polymer upon exposure to bodily fluids as in a vascular environment. Chemical degradation refers to degradation of a polymer due to chemical reaction of the polymer with bodily fluids or substances within bodily fluids. The chemical degradation can result in a decrease in molecular weight, deterioration of mechanical properties, and decrease in mass due to erosion. Mechanical properties may correspond to strength and modulus of the polymer. Deterioration of the mechanical properties of the polymer decreases the ability of a stent, for example, to provide mechanical support in a vessel. The chemical degradation can be the result of hydrolysis, oxidation, enzymolysis, and/or metabolic processes. Additionally, some bioabsorbable polymers are water soluble. A water soluble polymer corresponds to a polymer that is capable of dissolving in water in addition to, or even in the absence of chemical degradation of the polymer.

As indicated above, a stent made from a bioabsorbable polymer is intended to remain in the body for a duration of time until its intended function of, for example, maintaining vascular patency and/or drug delivery is accomplished. After the process of degradation, erosion, absorption, dissolution, and/or resorption has been completed, no portion of the bioabsorbable stent, or a bioabsorbable portion of the stent will remain. In some embodiments, very negligible traces or residue may be left behind. The duration can be in a range from about a month to a few years. However, the duration is typically in a range from about one month to twelve months, or in some embodiments, six to twelve months. It is important for the stent to provide mechanical support to a vessel for at least a portion of the duration. Many bioabsorbable polymers have erosion rates that make them suitable for treatments that require the presence of a device in a vessel for the above-mentioned time-frames.

As indicated above, it is desirable to have the capability of obtaining images of polymeric stents with x-ray fluoroscopy during and after implantation. Various embodiments of the present invention include stents with a coating having a radiopaque layer that includes radiopaque material to allow visualization of the stent with X-ray imaging. In some embodiments of the present invention, the radiopaque layer, including the radiopaque material, is bioabsorbable. A bioabsorbable radiopaque layer absorbs when it comes into contact with bodily fluids during delivery and after deployment of a stent at an implant site. Thus, the radiopaque layer may completely erode away along with the rest of the stent. Radiopaque material that is not bioabsorbable can be carried away by bodily fluids and eliminated from the body. The radiopaque layer can be configured to be visible a sufficient amount of time for delivery and implanting the stent. Additionally, the radiopaque layer allows radiopacity to be incorporated into the stent without significant deleterious affects to the mechanical integrity of the body or scaffolding of the stent.

Embodiments of a stent of the present invention include a bioabsorbable polymer body. In such embodiments, the bioabsorbable polymer of the body can be a non-water soluble hydrolytically degradable polymer. Representative examples of such polymers include poly(L-lactide), poly(DL-lactide), poly(glycolic acid), polycaprolactone, and copolymers thereof.

Figure 2A:
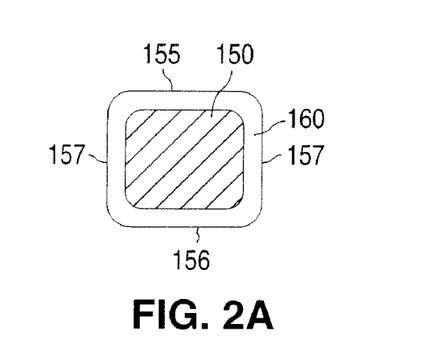
FIG. 2A depicts a cross-section of a strut with a coating.
Figure 2B:
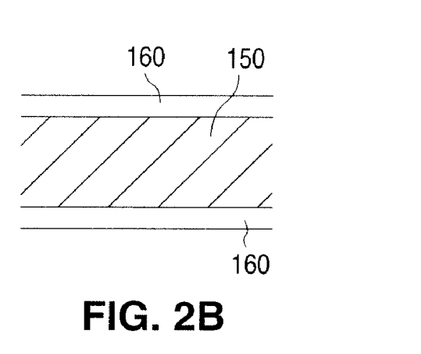
FIG. 2B shows an axial cross section of a strut with a coating from FIG. 2A.

In certain embodiments of the present invention, the stent includes a coating including a radiopaque layer above at least a portion of the bioabsorbable body. FIG. 2A depicts a cross-section of a strut 150 with a coating 160. FIG. 2B shows an axial cross section of strut 150 with coating 160. Coating 160 is shown to be on all surfaces of the strut, an abluminal surface 155, luminal 156, and sidewalls 157. However, in some embodiments, the coating can be disposed selectively on surfaces of strut 150. For example, the coating can be disposed selectively above abluminal surface 155, with other surface free of the coating.

Figure 3:
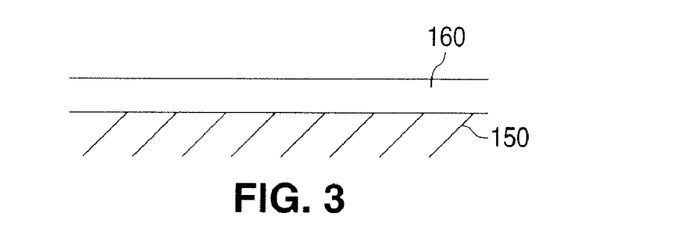
FIG. 3 depicts a close-up view of a surface of a strut with a radiopaque coating layer.

In some embodiments, a majority of the radiopaque layer is a contrast agent. In one embodiment, the contrast agent is water soluble. In certain embodiments, the radiopaque layer is all or substantially all a contrast agent. FIG. 3 depicts a close-up view of a surface of strut 150 with a contrast agent coating layer 160. Representative iodinated contrast agents may include, but are not limited to, acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, and combinations thereof. Contrast agents also include biocompatible metallic salts such as barium sulfate.

The contrast agent can be applied over a stent using various methods, such as, but not limited to, spraying or dip coating. An aqueous solution including a water soluble contrast agent can be prepared. The solution can then be sprayed on a stent using methods know to those of skill in the art. Alternatively, the stent can be dipped in the contrast agent solution. The stent can be air dried or dried in an oven. The spraying/dipping can be repeated a number of times to obtain a desired amount of contrast agent on the stent. In other embodiments, the contrast agent can also be applied as a powder. The stent can be dipped in an aqueous solution and contrast agent powder can be applied to the wet stent surface. The dipping and application can be repeated a number of times to obtain a desired amount of contrast agent on the stent.

As the stent is delivered and implanted, the water soluble contrast agent absorbs. In some embodiments, the radiopaque layer includes a sufficient amount of contrast agent to allow the stent to be visible for a selected period of time after implantation. Such a time can be ten minutes, one hour, two hours, ten hours, one day, one week, two weeks, or greater than two weeks. Although the implantation procedure may take only a few minutes, it can be advantageous to have the ability to locate the stent for a longer period of time after implantation. For example, problems may arise that may require the need to reintervene.

A radiopaque layer including all or mostly a contrast agent may dissolve faster than desired, thus, it may be advantageous to reduce the rate of absorption of a radiopaque layer. In further embodiments, the coating can include a radiopaque layer having a radiopaque agent dispersed within a bioabsorbable polymer. The radiopaque agent can include particles dispersed within the bioabsorbable polymer. The radiopaque agent can be biostable or bioabsorbable. The radiopacity of the layer can be controlled by the concentration of radiopaque agent in and thickness of the radiopaque layer.

Figure 4:
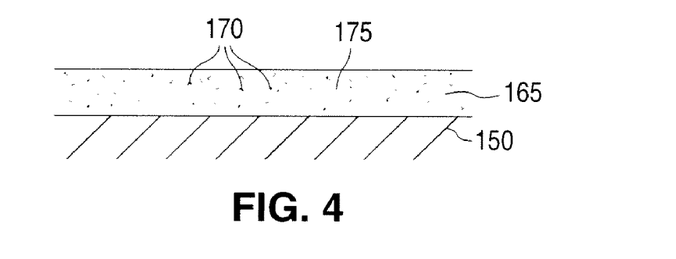
FIG. 4 depicts a close-up view of surface of a strut with a radiopaque coating layer including particles dispersed within a polymer.

FIG. 4 depicts a close-up view of a surface of strut 150 with a radiopaque coating layer 165 disposed above the surface. Radiopaque layer 165 includes particles 170 that are dispersed within a bioabsorbable polymer 175. As the bioabsorbable polymer erodes, particles of radiopaque agent are released. Additionally, bioabsorbable radiopaque particles can absorb prior to and after release from the layer. The life-time of the radiopaque layer can be controlled by the absorption rate of the bioabsorbable polymer and the thickness of the radiopaque layer.

The bioabsorbable polymer in the radiopaque layer can be the same or different from the bioabsorable polymer of the body of the stent. The required degradation time of a stent body and the time for visualization of a stent are generally different, with the former typically being longer than the latter. Thus, in some embodiments, the bioabsorbable polymer in the radiopaque layer can have a faster absorption rate than the bioabsorbable polymer body.

Generally, the life-time of the radiopaque layer can be controlled through selection of the bioabsorbable polymer in the radiopaque layer. In particular, the rate at which a layer absorbs can be tuned based on the selected time period, such as a time necessary to deliver a stent to an implant site or a longer period, such as the time needed for reintervention. In some embodiments, the bioabsorbable polymer in the radiopaque layer can be a non-water soluble hydrolytically degradable polymer. Examples of such polymers include poly(L-lactide) (PLLA), poly(DL-lactide) (PDLA), poly(glycolic acid) (PGA), poly(caprolactone) (PCL), and copolymers thereof. In one embodiment, the body of the stent can be a slower eroding polymer, such as PLLA, and the polymer in the radiopaque layer can be a faster eroding polymer, such as, PCL, PGA, or a copolymer thereof with PLLA. The content of faster eroding polymer in the copolymer can be modified to obtain a desired absorption rate.

In additional embodiments, the bioabsorbable polymer of the radiopaque layer can be a water soluble polymer. Exemplary water soluble polymers include poly(vinyl alcohol) (PVA) and poly(ethylene glycol) (PEG). Water soluble polymers tend to absorb faster than a non-water soluble hydrolytically degradable polymer. Thus, for a radiopaque layer of similar thickness, the radiopaque layer with a water soluble polymer can have a shorter life-time than a radiopaque layer with a non-water soluble hydrolytically degradable polymer.

PVA is both water soluble and hydrolytically degradable. The absorption rate of a layer of such polymers depends in part on the degree of hydrolysis of the water soluble polymer that is used in the layer.

In further embodiments, the bioabsorbable polymer can be a block copolymer including non-water soluble hydrolytically degradable blocks and water soluble blocks. The absorption rate, and thus, the life-time of the radiopaque layer can be controlled through the relative content of water soluble and non-water soluble hydrolytically degradable blocks. Water soluble blocks, such as PEG, absorb faster than non-water soluble hydrolytically degradable blocks and increase water content of the coating layer. Increasing the content of water soluble blocks increases absorption rate and decreases the life-time of the radiopaque layer. Alternatively, the life-time of a radiopaque layer can be increased by decreasing the content of the water soluble blocks.

Exemplary block copolymers can be a linear block copolymer having two or more blocks with at least one water soluble block and at least one non-water soluble hydrolytically degradable block, for example, a diblock copolymer or a triblock copolymer. Exemplary block copolymers can include, but are not limited to, PEG-PLLA, PEG-PDLA, PEG-PLGA, PEG-PLLA-PEG and PLLA-PEG-PLLA. The synthesis of such block copolymers is known in the art. For example, block copolymers of PLLA, PGA, and PLLAGA with PEG have been disclosed. Drug Delivery Technology, July/August 2003, Vol. 3 No. 5.

Figure 5A:
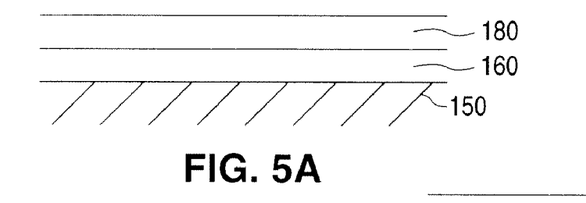
FIG. 5A depicts a topcoat layer above the contrast agent layer 160 of FIG. 3.
Figure 5B:
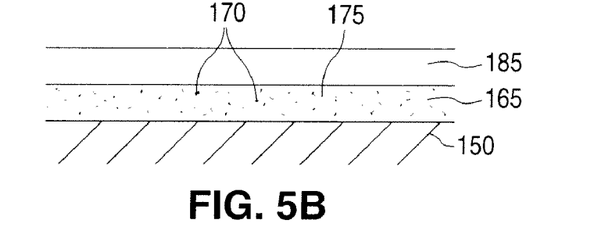
FIG. 5B depicts a topcoat layer above the radiopaque polymer/particle layer of FIG. 4.

In further embodiments, the stent can include a topcoat layer over the radiopaque layer. A topcoat layer can increase the life-time of a radiopaque layer by reducing or preventing absorption of the radiopaque layer for a period of time. The topcoat layer can be above a contrast agent layer or a polymer/particle radiopaque agent layer. FIG. 5A depicts a topcoat layer 180 over radiopaque contrast agent layer 160 of FIG. 3 and FIG. 5B depicts a topcoat layer 185 over radiopaque polymer/particle layer 165 of FIG. 4. The topcoat layer can be a water soluble polymer, non-water soluble hydrolytically degradable polymer, or a block copolymer including water soluble blocks and non-water soluble hydrolytically degradable blocks.

Figure 6A:
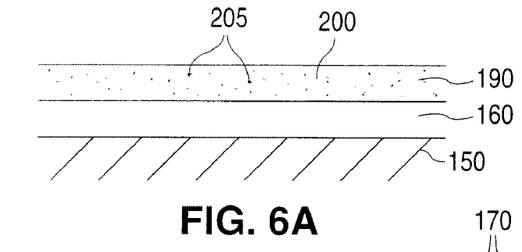
FIG. 6A depicts a drug-polymer layer above the contrast agent layer of FIG. 3.
Figure 6B:
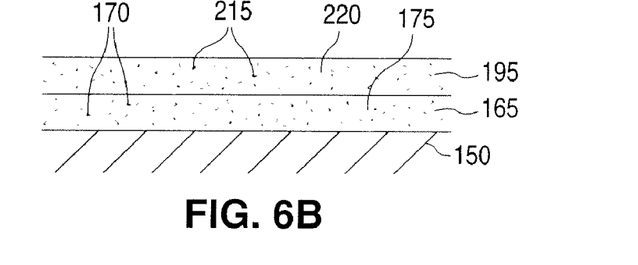
FIG. 6B depicts a drug-polymer layer above radiopaque polymer/particle layer of FIG. 4.

In additional embodiments, a coating above a stent can further include a drug-polymer layer in addition to the radiopaque layer. In such embodiments, the drug-polymer layer can be above the radiopaque layer. The drug-polymer layer can include a therapeutic agent or drug mixed or dispersed within a bioabsorable polymer. The drug-polymer layer can increase the life-time of a radiopaque layer, in addition, to delivering a drug to a lumen. FIG. 6A depicts a drug-polymer layer 190 over contrast agent layer 160 of FIG. 3. Drug-polymer layer 190 includes drug 205 dispersed within a bioabsorbable polymer 200. FIG. 6B depicts a drug-polymer layer 195 over radiopaque polymer/particle layer 165 of FIG. 4. Drug-polymer layer 195 includes a drug 215 dispersed within a bioabsorbable polymer 220. The bioabsorable polymer of the drug-polymer layer can be a water soluble polymer, non-water soluble hydrolytically degradable polymer, or a block copolymer including water soluble blocks and non-water soluble hydrolytically degradable blocks.

Figure 7A:
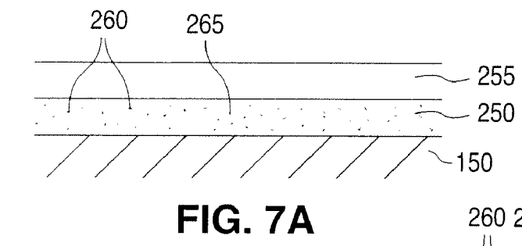
FIG. 7A depicts a close-up view of a surface of a strut with a drug-polymer layer above the surface with a contrast agent layer above the drug-polymer layer.
Figure 7B:
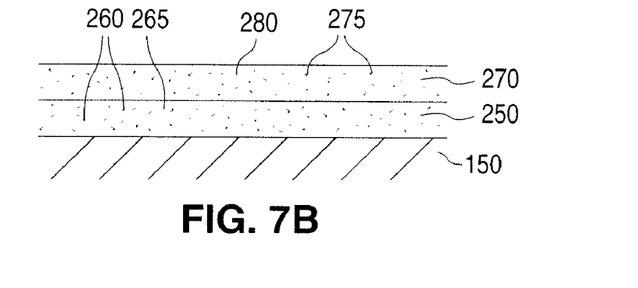
FIG. 7B depicts a close-up view of a surface of a strut with a drug-polymer layer above the surface with a radiopaque polymer/particle layer above the drug-polymer layer.

In an alternative embodiment of a stent with a drug-polymer layer, a radiopaque layer can be above the drug-polymer layer. In an embodiment, the radiopaque layer can be control the rate of elution of a drug from the drug-polymer layer to the lumen. FIG. 7A depicts a close-up view of a surface of a strut 150 with a drug-polymer layer 250 above strut 150. Drug polymer layer 250 includes drug 260 dispersed within bioabsorbable polymer 265. A contrast agent layer 255 is above drug-polymer layer 250. FIG. 7B depicts radiopaque polymer/particle layer 270 with radiopaque particles 275 dispersed within layer bioabsorbable polymer 280 in layer 270. Layer 270 is disposed over drug polymer layer 250 which has drug 265 dispersed within bioabsorbable polymer 265.

Figure 8A:
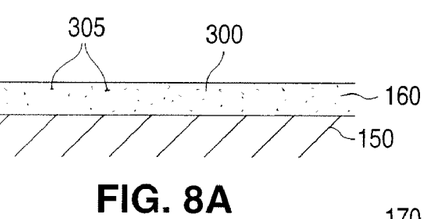
FIG. 8A depicts the contrast agent layer of FIG. 3 with a drug dispersed within the contrast agent layer.
Figure 8B:
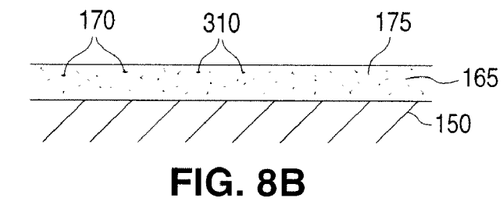
FIG. 8B depicts the radiopaque polymer/particle layer of FIG. 4 with a drug dispersed within the layer among radiopaque agent particles in a bioabsorbable polymer.

In other embodiments, the radiopaque layer can include a therapeutic agent or drug. Such embodiments can be useful in situations in which the visualization time of a stent is similar to the release time frame of the particular drug. FIG. 8A depicts contrast agent layer 160 of FIG. 3 with a drug 305 dispersed within layer 160. FIG. 8B depicts radiopaque polymer/particle layer 165 of FIG. 4 with a drug 310 dispersed within layer 165 among radiopaque agent particles 170 in bioabsorbable polymer 175.

Figure 9A:
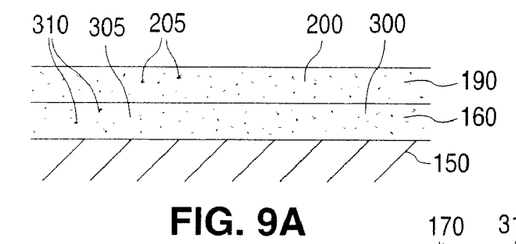
FIG. 9A depicts a drug-polymer layer above the contrast agent layer from FIG. 6A with a drug dispersed in the contrast agent layer.
Figure 9B:
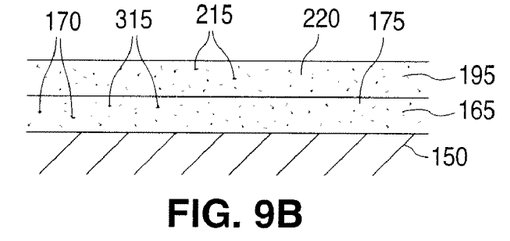
FIG. 9B depicts a drug-polymer layer above the radiopaque polyer/particle layer from FIG. 6B with a drug dispersed within a bioabsorbable polymer along with the radiopaque particles.

In additional embodiments, a stent can include a drug-polymer layer and a radiopaque layer with a drug within the radiopaque layer. FIG. 9A depicts drug-polymer layer 190 over contrast agent layer 160 from FIG. 6A with drug 310 dispersed in contrast agent 305 of layer 160. FIG. 9B depicts drug-polymer layer 195 above radiopaque polymer/particle layer 165 from FIG. 6B with drug 315 dispersed within bioabsorbable polymer 175 along with radiopaque particles 170.

Figure 10A:
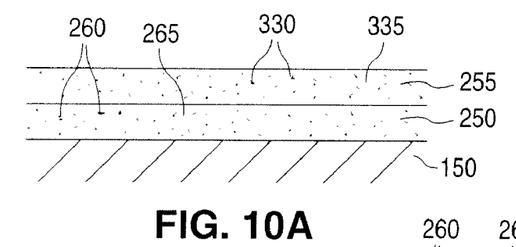
FIG. 10A depicts a contrast agent layer over the drug-polymer layer of FIG. 7A with a drug dispersed in the contrast agent.
Figure 10B:
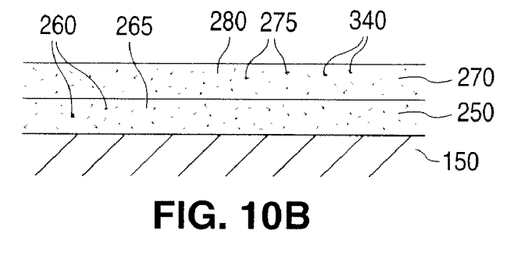
FIG. 10B depicts a radiopaque polymer/particle layer above the drug-polymer layer from FIG. 7B.

FIG. 10A depicts contrast agent layer 255 above drug-polymer layer 250 of FIG. 7A with drug 330 dispersed in contrast agent 335 of layer 255. FIG. 10B depicts radiopaque polymer/particle layer 270 above drug-polymer layer 250 from FIG. 7B. In radiopaque layer 270, drug 340 is dispersed within bioabsorbable polymer 280 along with radiopaque particles 275. In some embodiment, the drug in the radiopaque layer can be different from the drug in the drug-polymer layer. For example, the drug in an upper layer can be an antiproliferative or antiinflammatory drug and the drug in the lower layer can be an anticoagulant such as heparin.

A topcoat layer, radiopaque polymer/particle layer, or drug-polymer can be applies using methods know to those of skill in the art. Such methods include spraying or dipping.

Radiopaque agents mixed or dispersed within bioabsorbable polymers in radiopaque layers described above include contrast agents, biostable and erodible metals, metallic oxides, and biocompatible metallic salts. A radiopaque polymer layer can have a sufficient amount of radiopaque material to make the stent visible by X-ray imaging. The amount of radiopaque material can be adjusted obtain a desired degree of radiopacity. In one embodiment, the radiopaque material may be between 10% and 80%; 20% and 70%; 30% and 60%; or 40% and 50% by volume of the radiopaque layer. Additionally, the thickness of the radiopaque layer can be adjusted to obtain a desired degree of radiopacity or visibility.

Representative examples of metals that may be used as radiopaque agents include, but are not limited to, iron, magnesium, zinc, platinum, gold, and tungsten. Additionally, oxides of such metals and other metals may be used as radiopaque agents. In one embodiment, the metal can be erodible or corridible. An erodible or corrodible metal is one that has the propensity for self-dissolution in an in vivo environment. A metal that undergoes self-dissolution in an in vivo environment corrodes when subjected to bodily fluids and breaks down. A self-dissolving metal can be selected that has little or no ill effect to a patient. Representative examples of erodible metals include, but are not limited to, magnesium, zinc, tungsten, and iron.

A biocompatible metallic salt refers to a salt that may be safely absorbed by a body. Representative biocompatible metallic salts that may used in a radiopaque layer include, but are not limited to, ferrous sulfate, ferrous gluconate, ferrous carbonate, ferrous chloride, ferrous fumarate, ferrous iodide, ferrous lactate, ferrous succinate, barium sulfate, bismuth subcarbonate, bismuth potassium tartrate, bismuth sodium iodide, bismuth sodium tartrate, bismuth sodium triglycollamate, bismuth subsalicylate, zinc acetate, zinc carbonate, zinc citrate, zinc iodate, zinc iodide, zinc lactate, zinc phosphate, zinc salicylate, zinc stearate, zinc sulfate, and combinations thereof.

In some embodiments, the size the particles of radiopaque agent in a radiopaque layer can be small enough to reduce or eliminate the risk of thrombosis due to release of such particles from the coating. In particular, reducing the size of bioabsorbable particles decreases their absorption time. In one embodiment, a dimension of the particles can be 10-100 µm, 100-200 µm, or greater than 200 µm.

In certain embodiments, the radiopaque particles can be less than 10 µm. In particular, the particles can be nanoparticles. A "nanoparticle" refers to a particle with a dimension in the range of about 1 nm to about 100 nm. Another significant advantage smaller particles such as nanoparticles over larger particles is that nanoparticles may disperse more uniformly in a polymeric matrix, which results in more uniform radiopacity.

Embodiments of a radiopaque polymer/particle layer may be configured to be completely eroded in less than day, between a day and a week, between a week and a month, between a month and three months, between three months and six months, between 6 months and a year, or greater than 1 year.

Representative examples of polymers that may be used to fabricate embodiments of stents and coatings for stents of the present invention include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alpha-olefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

Drugs or therapeutic active agent(s) can include anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isofluprednone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, drugs or active can be other than antiproliferative agents or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammmatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin from Bristol-Myers Squibb Co., Stamford, Conn.). Examples of such antiplatelets, anticoagulants, anti-fibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic anti-thrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

The following example illustrates a stent with layer of contrast agent with no layer above the contrast agent layer. A common ionic contrast agent, (iohexol) was solubilized in water close to its saturation concentration. Iohexol is used broadly from coronary angiography to spinal cord imaging. A polymeric stent was dip coated in the aqueous solution and air-dried overnight. The dip coating process was repeated once. Once dry, the stent was visualized under a fluoroscope. A fluoroscopic image of the stent is shown in FIG. 11. Coated stents 400 and 410 are visible in FIG. 11.

Example 2

The following example illustrates a stent with a contrast agent layer with a PVA topcoat layer over the contrast agent layer. A 2 wt % solution of PVA (99+% hydrolyzed, MW~80,000) was prepared by adding approximately 0.5 grams PVA to 25 grams of water in a screw top glass bottle. The mixture was heated to approximately 90° C. for 30 minutes in order to dissolve the PVA. The mixture was labeled "Solution A" and left to stand overnight.

The following day, a 10 ml aliquot of Solution A was removed from the glass bottle and placed into a 20 ml glass vial. A total of 2 grams of contrast agent was added to this solution. Vigorous shaking was employed to get the contrast agent into solution. This second solution was labeled "Solution B."

An in-house 12 mm polymer stent (Abbott Cardiovascular Systems Inc., Santa Clara, Calif.) was coated with approximately 10 mg (weight prior to drying) of Solution B. A spray coater was used to coat the stent. The stent was then coated with approximately 2 mg of Solution A. The stent was dried under vacuum at room temperature for approximately 16 hours.

The stent was then visualized using a fluoroscope. FIGS. 12, 13, and 14 depict fluoroscopic images of the stent 450 before immersion in water, after being immersed in water for five minutes, and after being immersed in water for 15 minutes, respectively.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising:

a bioabsorbable polymer body composed of a scaffolding including a pattern of interconnected struts; and a coating above the bioabsorbable body, the coating comprising a radiopaque layer including a radiopaque agent dispersed within a second bioabsorbable polymer, wherein the coating comprises a topcoat layer above the radiopaque layer including a third bioabsorbable polymer, the third bioabsorbable polymer comprising a non-water soluble hydrolytically degradable polymer, a water soluble polymer, or a copolymer thereof, wherein the radiopaque agent has the ability to absorb X-rays and allows visualization of the stent with X-ray imaging.

2. A stent comprising:

a bioabsorbable polymer body composed of a scaffolding including a pattern of interconnected struts; and a coating above the bioabsorbable body, the coating comprising a radiopaque layer including a radiopaque agent dispersed within a second bioabsorbable polymer, wherein the coating further comprises a drug-polymer layer, and wherein the drug-polymer layer is above the radiopaque layer, wherein the radiopaque agent has the ability to absorb X-rays and allows visualization of the stent with X-ray imaging.

3. A stent comprising:

a bioabsorbable polymer body composed of a scaffolding including a pattern of interconnected struts; and a coating above the bioabsorbable body, the coating comprising a radiopaque layer including a radiopaque agent dispersed within a second bioabsorbable polymer, wherein the coating further comprises a drug-polymer layer, and wherein the radiopaque layer is above the drug-polymer layer, the radiopaque layer configured to reduce a rate of diffusion of a drug in the drug-polymer layer out of the coating, wherein the radiopaque agent has the ability to absorb X-rays and allows visualization of the stent with X-ray imaging.

4. A stent comprising:

a bioabsorbable polymer body composed of a scaffolding including a pattern of interconnected struts; and a coating above the bioabsorbable body, the coating comprising a radiopaque layer including a radiopaque agent dispersed within a second bioabsorbable polymer, wherein the coating further comprises a drug-polymer layer, and wherein the drug-polymer layer comprises a drug dispersed within a third bioabsorbable polymer, wherein the radiopaque agent has the ability to absorb X-rays and allows visualization of the stent with X-ray imaging.

5. The stent of claim 4, wherein the third bioabsorbable polymer comprises poly(DL-lactide).

6. A stent comprising:

a bioabsorbable polymer body composed of a scaffolding including a pattern of interconnected struts;

a coating above the bioabsorbable body, the coating comprising a radiopaque layer including a bioabsorbable polymer and a radiopaque agent dispersed within the bioabsorbable polymer, wherein a majority of the radiopaque layer is a water soluble contrast agent, and wherein the coating comprises a topcoat layer above the radiopaque layer including a bioabsorbable polymer, the bioabsorbable polymer comprising a non-water soluble hydrolytically degradable polymer or a water soluble polymer, wherein the radiopaque agent has the ability to absorb X-rays and allows visualization of the stent with X-ray imaging.

7. A stent comprising:

a bioabsorbable polymer body composed of a scaffolding including a pattern of interconnected struts;

a coating above the bioabsorbable body, the coating comprising a radiopaque layer including a bioabsorbable polymer and a radiopaque agent dispersed within the bioabsorbable polymer, wherein a majority of the radiopaque layer is a water soluble contrast agent, and wherein the coating comprises a drug-polymer layer above or below the radiopaque layer, the drug-polymer layer including a drug dispersed within a second dissolvable polymer, wherein the radiopaque agent has the ability to absorb X-rays and allows visualization of the stent with X-ray imaging.

* * * * *